United States Patent
Klink

[11] Patent Number: 5,877,742
[45] Date of Patent: Mar. 2, 1999

[54] MEDICAL IDENTIFICATION BRACELET

[76] Inventor: James Klink, 5377 Poola St., Honolulu, Hi. 96821-1536

[21] Appl. No.: 988,927

[22] Filed: Dec. 11, 1997

[51] Int. Cl.[6] .............................. G09G 5/34; G06F 15/09; G04B 47/00

[52] U.S. Cl. .................. 345/123; 345/905; 364/705.01; 364/708.1; 368/10

[58] Field of Search ............................... 345/1, 121, 123, 345/905, 973; 364/705.01, 708.1; 368/10, 281; 340/573, 825.54, 407.1

[56] References Cited

U.S. PATENT DOCUMENTS

| 4,819,860 | 4/1989 | Hargrove | 228/668 |
|---|---|---|---|
| 4,984,683 | 1/1991 | Elier | 206/38 |
| 5,012,229 | 4/1991 | Lennon | 340/706 |
| 5,168,480 | 12/1992 | Dodier | 368/282 |
| 5,337,290 | 8/1994 | Ventimiglia | 368/10 |
| 5,488,571 | 1/1996 | Jacobs et al. | 364/705 |
| 5,535,147 | 7/1996 | Jacobs et al. | 364/705.07 |
| 5,570,297 | 10/1996 | Brzezinski et al. | 364/705.07 |
| 5,649,381 | 7/1997 | Studer | 368/281 |
| 5,652,570 | 7/1997 | Lepkofker | 340/573 |
| 5,771,399 | 6/1998 | Fishman | 395/892 |

Primary Examiner—Jeffery Brier
Assistant Examiner—David L. Lewis

[57] ABSTRACT

The present invention is a traditional, yet more stylish, medical identification bracelet which has electronic circuitry to display detailed, patient medical information. The bracelet is formatted using a programming station (PC) into which is entered up to 16 k bits of medical & personal information about an individual. The programming station transfers the formatted information to the bracelet via an infra-red interface device. The medical identification bracelet has an LCD view screen which displays, in a scrolling fashion, data when a button is pushed. The information may be scrolled in either direction, paused and set to free run. All information is available at the display. The character size is selected to be visible to the unaided eye. The display is illuminated for low light reading.

14 Claims, 7 Drawing Sheets

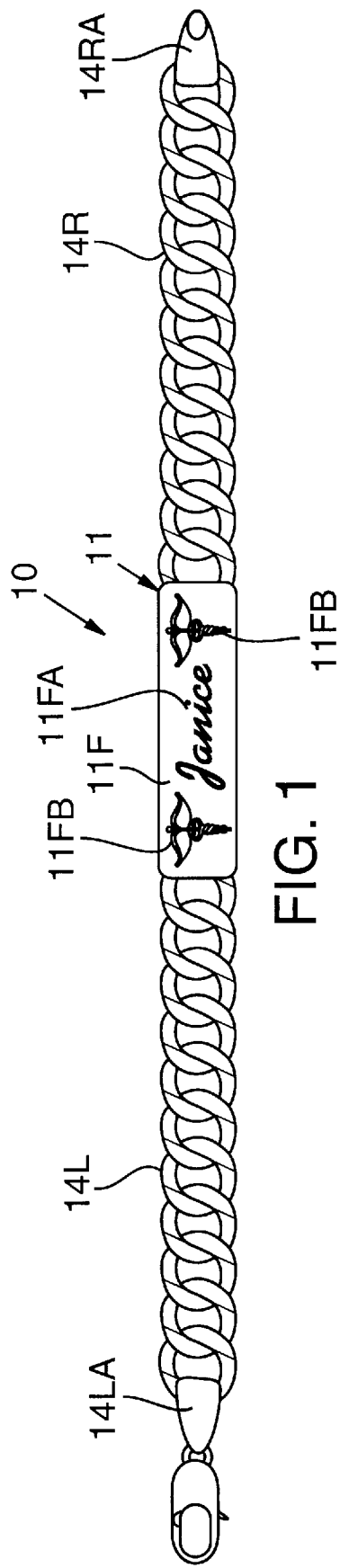
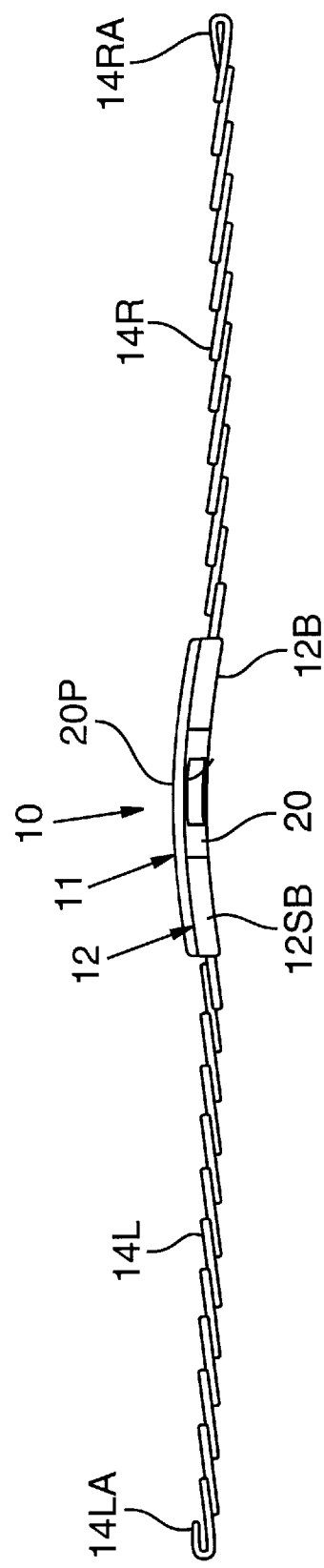
FIG. 1
FIG. 1A

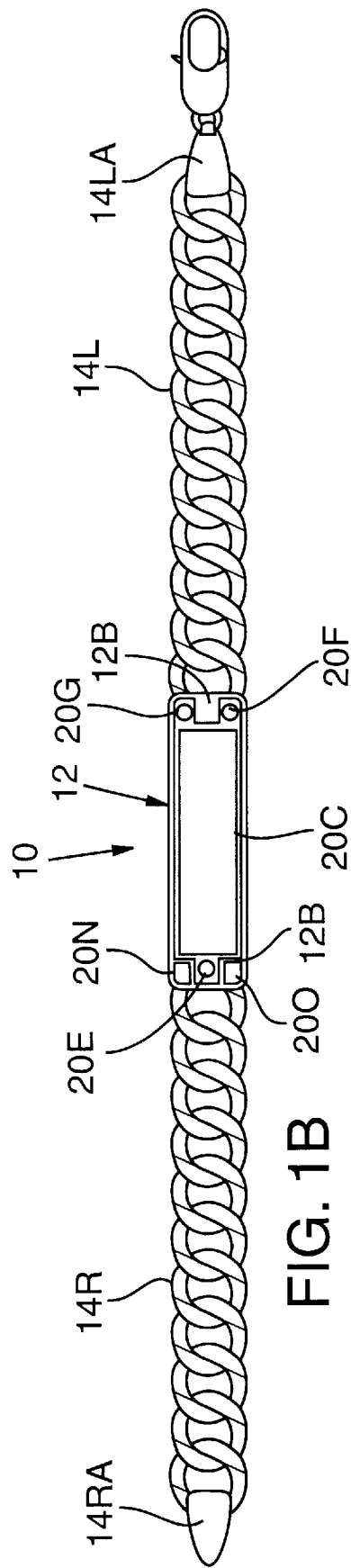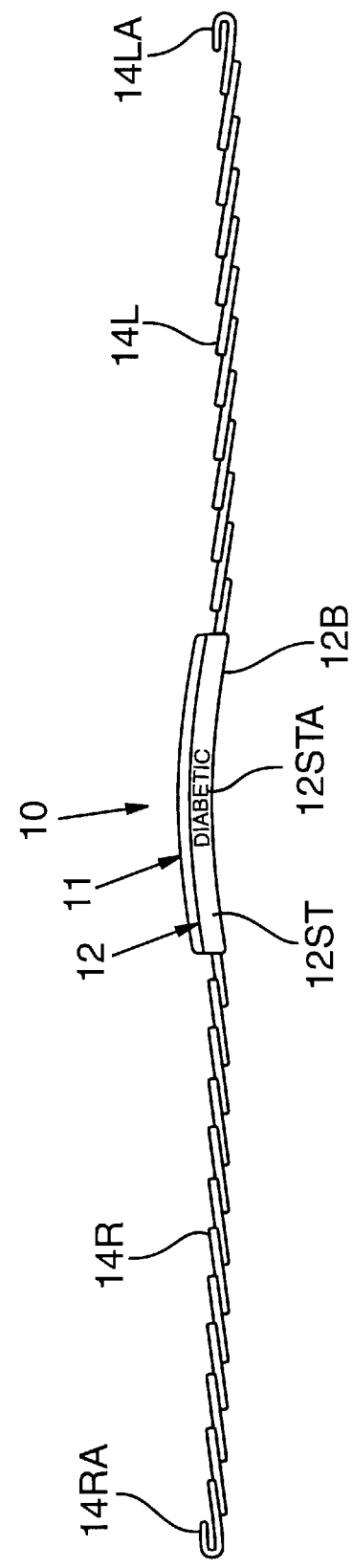
FIG. 1B
FIG. 1C

MEDICAL IDENTIFICATION BRACELET

BACKGROUND OF THE INVENTION

1. Field of the Invention

The present invention relates to identification devices. More particularly, the present invention relates to identification jewelry which has electronic circuitry to display medical information about the wearer.

2. Description of the Prior Art

In emergency situations when the patient is unconscious, medical information may be critical to a patient's survival. This is especially important when the patient is an accident victim and is unattended. Emergency medical personnel need basic information to begin treatment of a patient. Identification tags and devices in the past have been disclosed which contain finely printed information that is read by emergency medical personnel using an optical magnifier. The information is limited by the ability to print the information small enough so that a sufficient volume of data can be retained. Similarly, electronic devices such as a healthwatch, smart cards, and optical disks have been disclosed which contain medical information that is read by a reader. Both types of inventions require an auxiliary device to make all the information available to emergency medical personnel. What is needed is a device that shows detailed information without requiring a reading device and that can be simply set up using a basic personal computer.

Numerous innovations for a Medical Identification Bracelet have been provided in the prior art that are described as follows. Even though these innovations may be suitable for the specific individual purposes to which they address, they differ from the present invention as hereinafter contrasted.

In U.S. Pat. No. 5,488,571, titled Method and Apparatus for Downloading Information from a Controllable Light Source to a Portable Information Device, invented by Michael A. Jacobs and Mark A. Insero, a system is described for transferring data from a CRT (cathode ray tube) video display monitor on a personal computer to a portable information device such as a multifunction electronic wristwatch. The CRT video display has a video signal generator providing raster scanning of the screen and a program for formatting the binary coded data into blocks of serial data bits, with start bit and stop bit. The blocks of data are supplied to the video signal generator in synchronism with raster scanning of the screen so as to provide an integral number of one or more blocks of data for each vertical frame, and modulated to vary the brightness of the screen and provide light pulses corresponding to presence or absence of binary coded transmitter pulses. The portable information device is manipulated within line of sight of the CRT screen and has a photosensor to detect light pulses when the photosensor is directed toward the screen. Signals from the photosensor are amplified and filtered to remove ambient light source flicker and extraneous spurious light signals and to convert the receiver pulses to binary coded data blocks varying between high and low logic levels at a preselected pulse repetition rate. The portable information device stores the received data for further use.

The patented invention differs from the present invention because the patented invention is a system which transfers data from a CRT (cathode ray tube) video display monitor on a personal computer to a portable information device without a physical connection. The patented invention has a photodiode sensor which is connected to electronic circuitry that permits the photodiode to 'read' the information on the CRT video display monitor. The photodiode and electronic circuitry may be contained within a wrist watch device. The patented invention lacks the features of display of medical information, scrolling of the stored information in either direction, scroll pause, and free running display of information, all of which are included in the present invention.

In U.S. Pat. No. 5,337,290, titled Health Watch, invented by Phillip Vestimiglia and Louis E. Sansone, access to critical medical data is addressed. The Health Watch is worn like a conventional wrist watch and contains two levels of data. The first level, which contains the most critical medical data, can be displayed on the watch's alphanumeric display screen. The second level of data, which is of lower priority and is frequently more detailed, can be accessed only by an external data terminal via a serial data port on the watch. The watch combines all circuitry including memory into a single application specific integrated circuit. An update mode provides a means of updating the medical data.

The patented invention differs from the present invention because the patented invention is a watch device having an alphanumeric display which shows a user specific information. At least two lines of data are displayed which is selected from but not limited to a group consisting of time, chronograph, medical data, logo, and personal information. Displayed information may be scrolled by pressing a switch. Data is also accessible to an external interface which must be hardwired to a computer using a protocol well known in the art. The data output includes but is not limited to family history, history of illness, immunization history, history of major operations, and results of previous major tests. Accessing this information requires a compatible interface. The data is loaded into the patented invention via the external interface. The patented invention functions as a wrist watch when it is not displaying medical data.

The present invention is a programming station into which is entered medical and personal information about an individual. The programming station formats and transfers the formatted information to a bracelet having comparable interface circuitry adapted for this purpose. The bracelet has a three line alphanumeric display which, when a button is pushed, scrolls through the recorded information. All information is available to the user or reader and includes but is not limited to personal information, medications and dosages taken, family history, history of illness, allergies, immunization history, history of major operations, insurance information, physician and pharmacy names and numbers, what to do in an emergency, next of kin, and results of previous major tests. The present invention uses an IR data link to the computer which eliminates the use of wires.

In U.S. Pat. No. 5,168,480, titled Watch Accessory, invented by Louise Dodier, a wrist-watch accessory is described comprising a hollow open-ended cylinder and a pair of flat spaced-apart, generally parallel legs protruding from one side of the cylinder in superposed relation. The loop of the wrist band of the watch has an opening in which the cylinder is inserted to surround the push pin retaining the wrist band to the wrist-watch. The outer and inner legs are in contact with the outer and inner faces of the wrist band. A decoration can be applied on the outer leg. Either one of the two legs can bear an identification or Medic Alert label.

The patented invention differs from the present invention because the patented invention is a mechanical device bearing a Medic Alert logo. The device is not electronic. The imprinting of medical information other than the Medic Alert logo is not disclosed.

In U.S. Pat. No. 5,012,229, titled User Wearable Personal/ Medical Information Device, invented by Charles A. Lennon and George Lowe, a wearable personal/medical information device is described which includes a data display with an associated legend display. A memory stores items of personal and/or medical information relating to the person wearing the device. Upon operation of a switch, the stored information is displayed with the personal/medical information indicated by the data display, and a corresponding legend indicated by the legend display. In a preferred embodiment, certain data such as medical information is preset in a read only memory, and other data which the user may change from time-to-time is stored in a read/write memory.

The patented invention differs from the present invention because the patented invention includes a time date display an d an information display. The displayed information may be cycled automatically or manually but not scrolled. As the information must be displayed in groups of 16, limited information is available to a user. Further, to conserve characters, information must be displayed in a form of code or abbreviation, albeit easily understood. Since the present invention scrolls the information, it is not limited to a specific number of characters per data item. Since the present invention is not limited as to the characters per data item clear descriptions can be provided rather than coded word as is done in the patented invention.

In U.S. Pat. No. 4,984,683, titled Fine Jewelry Enclosing Wearer Identification and Medical Information Therein, invented by Audrey L. Eller, a decorative piece of personnel jewelry is described which includes a locket, worn around the neck of the user on a chain or a bracelet worn on the wrist of the user. A compartment within the piece of jewelry contains an attached identification and medical history of the wearer. The attached document is constructed of a water proof paper or the like and when the paper extends beyond the edge of the jewelry, the medical history and identification of the wearer is revealed. The document is fan folded within the compartment and concealed from an observer of the jewelry when the jewelry is worn. A symbol recognizable by trained, medical personnel is positioned in a prominent location on the outer surface of the jewelry.

The patented invention differs from the present invention because the patented invention is an item of jewelry comprising a case having medical information recorded on printed media contained therein. The present invention is an electronic device with a nonvolatile memory which displays information on demand. The patented invention is a manual device. The present invention is electronic.

In U.S. Pat. No. 4,819,860, titled Wrist-Mounted Vital Functions Monitor and Emergency Locator, a wrist-mounted pulse rate and body temperature monitor has means for storing upper and lower emergency pulse rates and body temperatures by means of which an emergency medical situation is defined. When the monitor detects an emergency medical situation, an emergency signal is generated on standard emergency locator frequencies to alert search and rescue services. Means for automatically setting the upper and lower safe thresholds is provided. The device is particularly suited for use by individuals in remote areas where either the health of the individual or the environment create a higher risk to the survival of the individual.

The patented invention differs from the present invention because the patented invention is a real time monitor for vital signs which transmits data via a radio link to a monitoring station. Electronic circuits sense critical vital signs variations beyond a preselected value and initiate an alarm sequence. A display is not disclosed. Text information is not displayed or transmitted.

The above patented inventions differ from the present invention because they fail to describe or claim at least one combination of the following features depicted in the present invention. The present invention has a programming station into which is entered medical & personal information about an individual. The programming station formats and transfers the formatted medical information to a bracelet. The bracelet has electronic circuitry which scrolls the medical information across the display when a button is depressed. The information may be scrolled in either direction, paused, and set to free run. It can be modified or updated as needed.

Numerous innovations for Medical Identification Bracelets have been provided in the prior art that are adapted to be used. Even though these innovations may be suitable for the specific individual purposes to which they address, they would not be suitable for the purposes of the present invention as heretofore described.

SUMMARY OF THE INVENTION

The present invention is a traditional, yet more stylish, medical identification bracelet or pendant which has electronic circuitry to display patient medical information. The bracelet is set up using a programming station (PC) into which is entered up to 16 k bits of medical & personal information about an individual. The programming station formats and transfers the formatted information to a bracelet via an interface device. The bracelet has an LCD view screen display which displays, in a scrolling fashion, data when a button is pushed. The information may be scrolled in either direction, paused and set to free run. All information is available at the display. The character size is selected to be visible to the unaided eye. The display is illuminated for low light reading.

Among the types of problems encountered in the prior art, the foremost focuses on providing detailed medical information to emergency medical treatment personnel. Better information enables physicians to provide medical care that is less expensive and less error prone. The prescription of medications is more accurate when attending physicians know what medications and dosages the victim is taking and has taken in the past. The ordering of needless clinical tests and exams is also reduced in number and cost, and the requesting of precise retesting is more likely when physicians have before them information about previous testing and the medical history of their patient which this present invention provides.

In the prior art, unsuccessful attempts to solve this problem were attempted namely: dog tags, lockets with printed information, printed information contained on a bracelet which is read using a magnifying glass, and electronic devices from which the information can be read using an auxiliary reader. However, the problem was solved by the present invention because the medical information is scrolled on an LCD display with a type size sufficient to be read by the unaided eye. The information is programed into the present invention by a simple personal computer driven programing station.

Innovations within the prior art are rapidly being exploited with the ability to provide medical information to emergency personnel when the patient is unconscious.

The present invention went contrary to the teaching of the art because the information is available without an auxiliary device for reading the information.

The present invention solved a long felt need for detailed information about an accident victim available at the accident scene. The first person arriving in an emergency situation or making the initial phone call to a hospital or EMT service will be able with the present invention to provide critical and detailed medical information about that victim. The hospital or EMT crew can now be in an optimal position to better prepare their emergency room, operating room, or ambulance with any special supplies, equipment, or medications which may be required to deliver the best possible aid in the shortest possible time.

Accordingly, it is an object of the present invention to provide a cosmetically pleasing and more stylish article. It is also an object of the present invention to provide an electronic device having a display means which scrolls medical information.

In keeping with these objects, and with others which will become apparent hereinafter, one feature of the present invention, succinctly stated, is that it resembles a fashionable, Medic Alert bracelet on one side which has an LCD display on the reverse.

When the medical identification bracelet is designed in accordance with the present invention, electronic circuitry receives medical data from a programming device (PC).

In accordance with another feature of the present invention, a data transfer device is peripherally connected to a personal computer. The data transfer device functions to transfer preselected medical data to the medical identification bracelet or, data from the medical identification bracelet to the user's personal computer.

Another feature of the present invention is that a housing framework secures an electronic hardware module to the medical identification bracelet.

Still another feature of the present invention is an LCD which shows medical and personal information in a scrolling format.

Yet still another feature of the present invention is that a control means provides for forward, halt and backwards scrolling.

The novel features which are considered characteristic for the invention are set forth in the appended claims. The invention itself however, both as to its construction and its method of operation, together with additional objects and advantages thereof, will be best understood from the following description of the specific embodiments when read and understood in connection with the accompanying drawings.

LIST OF REFERENCE NUMERALS UTILIZED IN THE DRAWINGS

10—medical identification bracelet (10)
11—precious metal bar (11)
11F—precious metal bar front (11F)
11FA—precious metal bar front name indicia (11FA)
11FB—precious metal bar front medical symbol (11FB)
12—housing (12)
12B—housing back fastener (12B)
12ST—housing top side (12ST)
12STA—housing top side medical condition indicia (12STA)
12SB—housing bottom side (12SB)
14L—left holding means (14L)
14LA—left holding means fastener (14LA)
14R—right holding means (14R)
14RA—right holding means fastener (14RA)
16—data transfer device (16)
16A—data transfer device housing (16A)
16F—data transfer device front (16F)
16B—data transfer device back (116B)
16L—data transfer device left side (16L)
16LA—data transfer device left side slot (16LA)
16R—data transfer device right side (16R)
16RA—data transfer device right side slot (16RA)
16D—data transfer device cable (16D)
16DA—data transfer device cable connector (16DA)
20—bracelet electronics module (20)
20A—bracelet electronics module microcontroller (20A)
20AA—bracelet electronics module microcontroller ON/OFF, backlight input (20AA)
20AB—bracelet electronics module microcontroller mode/send/receive input (20AB)
20AC—bracelet electronics module microcontroller scroll/pause/back input (20AC)
20AD—bracelet electronics module microcontroller memory input/output (20AD)
20AE—bracelet electronics module microcontroller receiver input (20AE)
20AF—bracelet electronics module microcontroller transmit output (20AF)
20B—bracelet electronics module memory (20B)
20C—bracelet electronics module alphanumeric display (20C)
20CA—bracelet electronics module alphanumeric display indicia (20CA)
20D—bracelet electronics module DC/DC converter (20D)
20E—bracelet electronics module ON/OFF, backlight switch (20E)
20F—bracelet electronics module mode/send/receive switch (20F)
20G—bracelet electronics module scroll/pause/back switch (20G)
20H—bracelet electronics module sending photodiode (20H)
20I—bracelet electronics module receiver unit (20I)
20IA—bracelet electronics module receiver unit pull up resistor (20IA)
20IB—bracelet electronics module receiver unit transistor (20IB)
20IC—bracelet electronics module receiver unit bias resistor (20IC)
20ID—bracelet electronics module receiver unit receiver photodiode (20ID)
20J—bracelet electronics module first pull up resistor (20J)
20K—bracelet electronics module second pull up resistor (20K)
20L—bracelet electronics module third pull up resistor (20L)
20M—bracelet electronics module LED/photodiode interface circuitry (20M)
20N—bracelet electronics module photosensor canopy (20N)
20O—bracelet electronics module LED canopy (20O)
20P—bracelet electronics module battery cover (20P)
22—data transfer device electronics module (22)
22A—data transfer device electronics module microcontroller (22A)
22B—data transfer device electronics module memory (22B)
22C—data transfer device electronics module LED/photodiode interface circuitry (22C)
22D—data transfer device electronics module transmitter (22D)
22E—data transfer device electronics module data receiver (22E)
22F—data transfer device electronics module computer interface (22F)

22G—data transfer device electronics module power regulator (22G)

24—power source (24)

BRIEF DESCRIPTION OF THE DRAWINGS

FIG. 1 is a front view of a medical identification bracelet.

FIG. 1A is a bottom side view of a medical identification bracelet.

FIG. 1B is a back view of a medical identification bracelet.

FIG. 1C is a top side view of a medical identification bracelet.

DESCRIPTION OF THE PREFERRED EMBODIMENT

Figure 2:
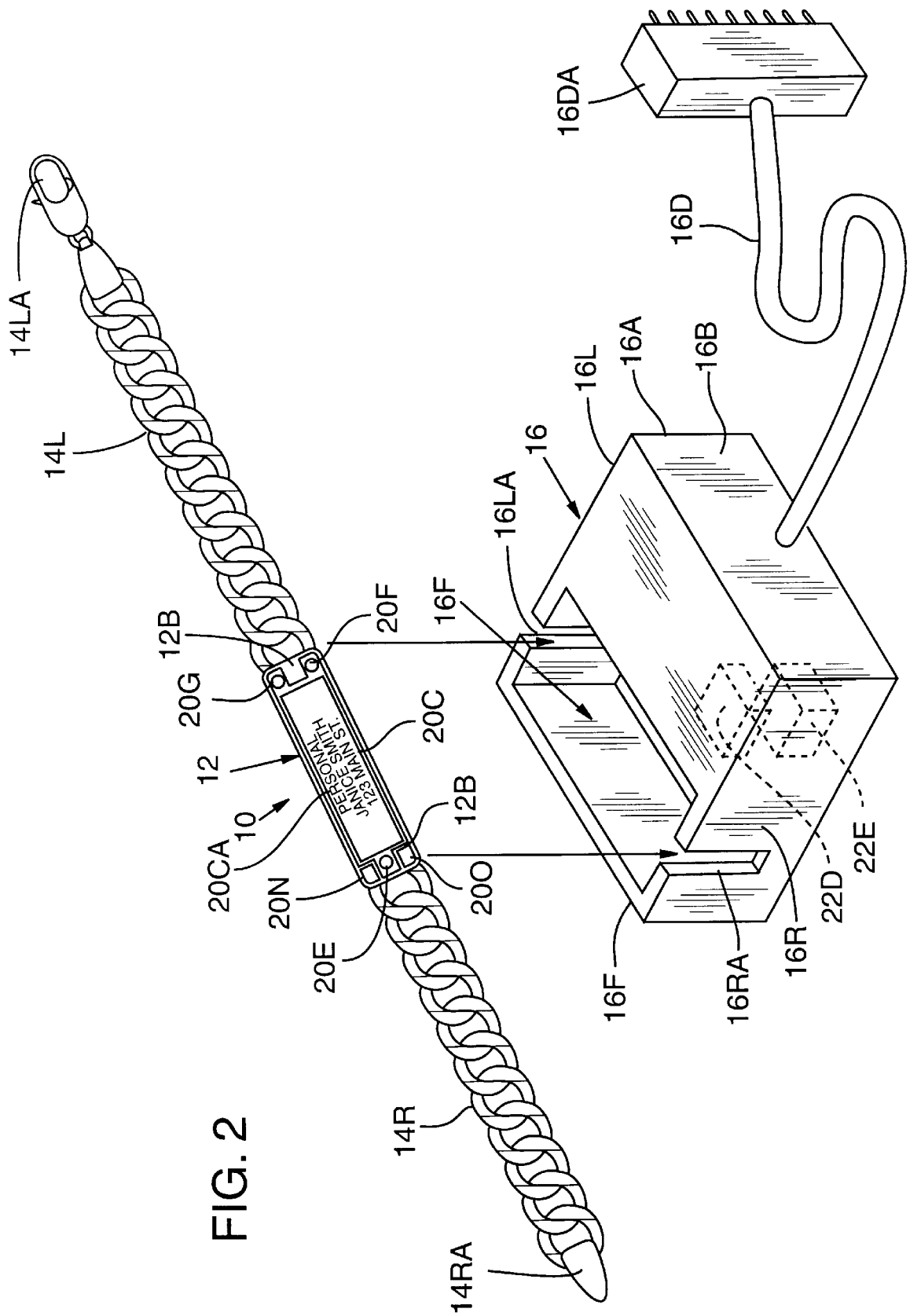
FIG. 2 is a perspective view of a medical identification bracelet showing a data transfer device.

Firstly, referring to FIG. 1, FIG. 1A, FIG. 1B, and FIG. 1C which show a medical identification bracelet (10). The medical identification bracelet (10) comprises a housing (12), having a housing top side (12ST) having a housing top side medical condition indicia (12STA) thereon and a housing bottom side (12SB) housing back fasteners (12B) are made part of the housing (12) which functions to hold the bracelet electronics module (20) firmly in position.

The housing (12) is attached to the bracelet precious metal bar (11) which comprises a precious metal bar front name indicia (11FA) which functions to display the user's name. The bracelet precious metal bar (11) further comprises a precious metal bar front symbol (11FB) functioning to indicate the medical identificaion bracelet (10) contains medical information.

The bracelet precious metal bar (11) further comprises a holding means (14) securely attached to opposite ends of the bracelet precious metal bar (11). The holding means (14) functions to removably fasten the bracelet precious metal bar (11) to a user's body. The holding means (14) comprises a left holding means (14L), one distal end of the left holding means (14L) is securely attached to one distal end of the bracelet precious metal bar (11). The opposite distal end of the left holding means (14L) is securely attached to a left holding means fastener (14LA). The opposite distal end of the bracelet precious metal bar (11) is securely attached to one distal end of a right holding means (14R). The opposite distal end of the right holding means (14R) is securely attached to a right holding means fastener (14RA). The left holding means fastener (14LA) and right holding means fastener (14RA) are removably fastened together. The left holding means fastener (14LA) and the right holding means fastener (14RA) are selected from a group consisting of hook & loop, hook & eye, buckle, snaps, and button/hole.

The left holding means (14L), left holding means fastener (14LA), right holding means (14R), and right holding means fastener (14RA) are manufactured from materials selected from a group consisting of plastic, ceramic, plastic composite, metal, metal alloy, precious metal, gems, and wood.

Now referring to FIG. 2 which is a perspective view of a medical identification bracelet (10) showing a data transfer device (16). The data transfer device (16) which comprises a data transfer device housing (16A) which comprises a data transfer device front (16F) which is securely attached on one distal end to a front distal end of a data transfer device left side (16L) having a data transfer device left side slot (16LA) therein. The data transfer device front (16F) on an opposite distal end is securely attached to a front distal end of a data transfer device right side (16R) having a data transfer device right side slot (16RA) therein. The data transfer device right side slot (16RA) and the data transfer device left side slot (16LA) function to removably fasten the bracelet electronics module microcontroller (20A) therebetween. A back distal end of the data transfer device left side (16L) is securely attached to one distal end of a data transfer device back (16B). The opposite distal end of the data transfer device back (16B) is securely attached to a back distal end of the data transfer device right side (16R).

The data transfer device (16) further comprises a data transfer device electronics module (22) which comprises a data transfer device electronics module microcontroller (22A) which is electrically connected to a data transfer device electronics module memory (22B) that functions to store an operating program and data.

The data transfer device electronics module microcontroller (22A) is further electrically connected by data transfer device electronics module LED/photodiode interface circuitry (22C) to a transfer device electronics module transmitter (22D) which functions to send data to the bracelet electronics module receiver unit (20I).

The data transfer device electronics module microcontroller (22A) is further electrically connected by means of the data transfer device electronics module LED/photodiode interface circuitry (22C) to a data transfer device electronics module data receiver (22E) functioning to receive data from the bracelet electronics module sending photodiode (20H).

The data transfer device electronics module microcontroller (22A) is further electrically connected to a data trasfer device electronics module computer interface (22F) which functions to send and receive data to a data transfer device cable (16D). The data transfer device cable (16D) is electronically connected to a computer by a data transfer device cable connector (16DA).

Figure 3:
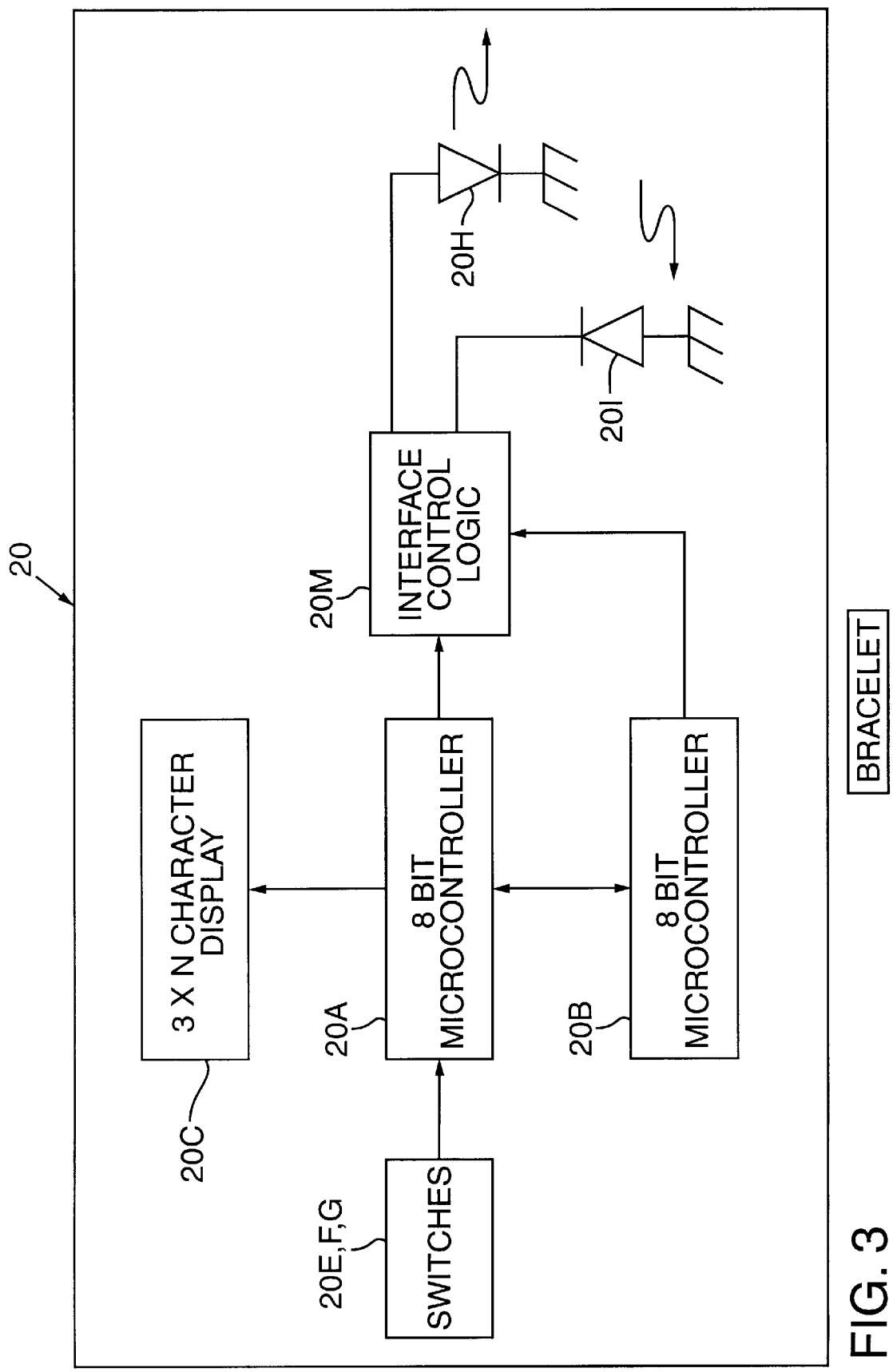
FIG. 3 is a block diagram of a bracelet electronics module.
Figure 4:
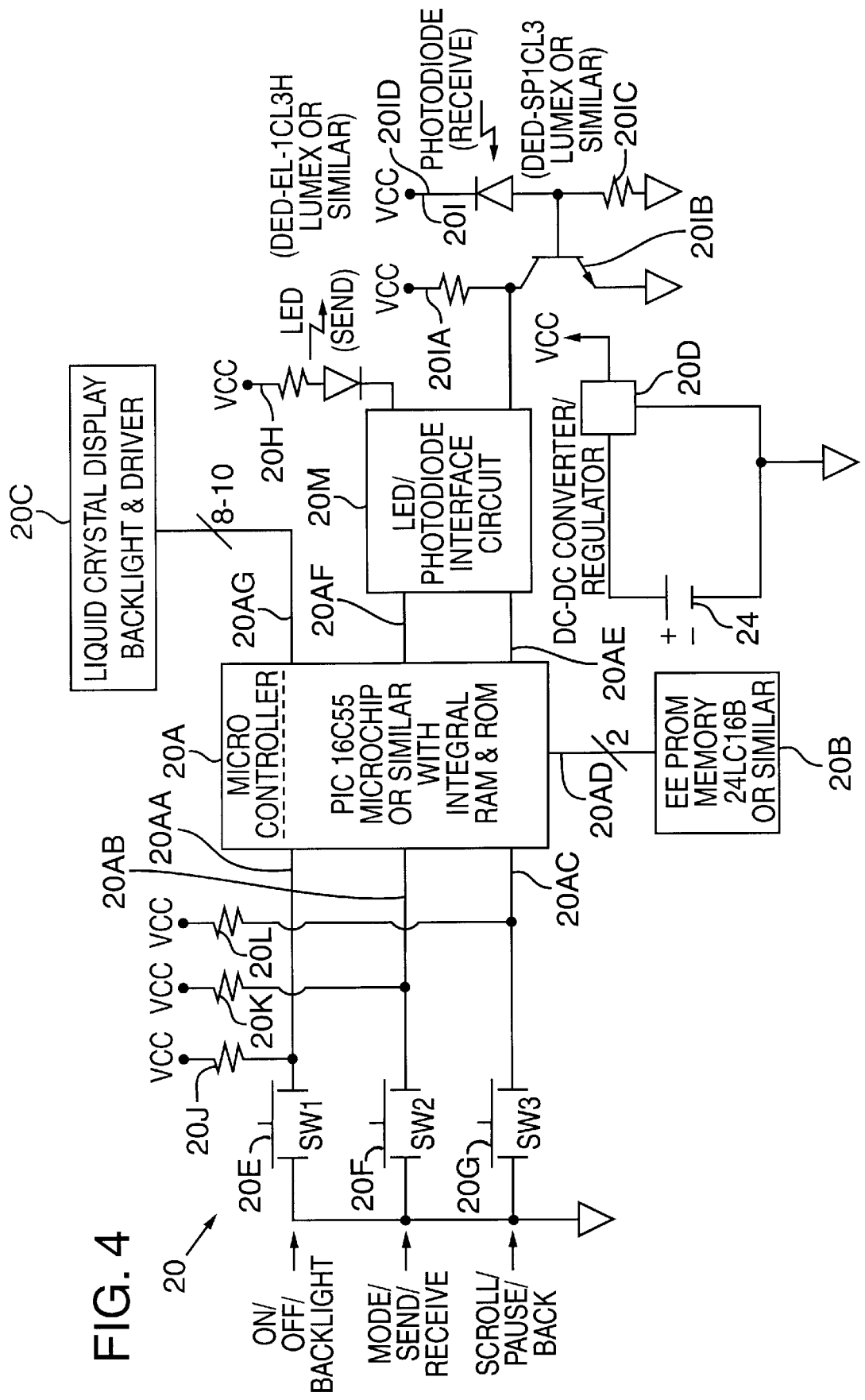
FIG. 4 is a schematic diagram of a bracelet electronics module.

Thirdly, referring to FIG. 3 which is a block diagram of a bracelet electronics module (20) and FIG. 4 which is a schematic diagram of a bracelet electronics module (20). The bracelet electronics module (20) comprises a bracelet electronics module microcontroller (20A) which is electrically connected to a bracelet electronics module memory (20B) functioning to store data. The bracelet electronics module microcontroller (20A) is further electrically connected to a bracelet electronics module alphanumeric display (20C) which functions to display bracelet electronics module alphanumeric display indicia (20CA) selected from the bracelet electronics module memory (20B). The bracelet electronics module microcontroller (20A) is further electrically connected to a bracelet electronics module DC/DC converter (20D) functioning to convert a voltage from a power source to a voltage usable by the bracelet electronics module (20). The bracelet electronics module microcontroller (20A) further comprises a bracelet electronics module microcontroller ON/OFF, backlight input (20AA) which is electrically connected to a bracelet electronics module ON/OFF, backlight switch (20E) which functions to activate illumination of the bracelet electronics module alphanumeric display (20C) when the bracelet electronics module (20) is turned on and exhibits the bracelet electronics module alphanumeric display indicia (20CA) which can be observed when ambient lighting is low.

The bracelet electronics module microcontroller backlight input (20AA) is electrically connected to one distal end of a bracelet electronics module first pull up resistor (20J). The opposite distal end of the bracelet electronics module first pull up resistor (20J) is electrically connected to the bracelet electronics module DC/DC converter (20D). The bracelet electronics module first pull up resistor (20J) functions to keep the bracelet electronics module microcontroller ON/OFF, backlight input (20AA) at a preselected voltage when the bracelet electronics module ON/OFF, backlight switch (20E) is not depressed.

The bracelet electronics module microcontroller (20A) further comprises a bracelet electronics module microcontroller mode/send/receive input (20AB) which is further electrically connected to a bracelet electronics module mode/send/receive switch (2F) connecting the bracelet electronics module microcontroller mode/send/receive input (20AB) to an electrical ground.

The bracelet electronics module microcontroller mode/send/receive input (20AB) is electrically connected to one distal end of a bracelet electronics module second pull up resistor (20K). The opposite distal end of the bracelet electronics module second pull up resistor (20K) is electrically connected to the bracelet electronics module DC/DC converter (20D). The bracelet electronics module second pull up resistor (20K) functions to keep the bracelet electronics module microcontroller mode/send/receive input (20AB) at a preselected voltage when the bracelet electronics module mode/send/receive switch (20F) is not depressed.

The bracelet electronics module mode/send/receive switch (20F) functions to switch the bracelet electronics module alphanumeric display (20C) to display preselected groupings of bracelet electronics module alphanumeric display indicia (20CA). The preselected grouping of information is selected from a group consisting of personnel data, medical conditions, medications & dosages, allergies, insurance company information, patient history, next of kin, pharmacy and physician names and phone numbers, previous illnesses, blood type and pressure. The bracelet electronics module mode/send/receive switch (20F) further functions to switch between functions selected from a group consisting of display information, transmit data and receive data.

The bracelet electronics module microcontroller (20A) further comprises a bracelet electronics module microcontroller scroll/pause/back input (20AC) electrically connected to a bracelet electronics module scroll/pause/back switch (20G) connecting the bracelet electronics module microcontroller scroll/pause/back input (20AC) to the electrical ground.

The bracelet electronics module microcontroller scroll/pause/back input (20AC) is electrically connected to one distal end of a bracelet electronics module third pull up resistor (20L). The opposite distal end of the bracelet electronics module third pull up resistor (20L) is electrically connected to the bracelet electronics module DC/DC converter (20D). The bracelet electronics module third pull up resistor (20L) functions to keep the bracelet electronics module microcontroller scroll/pause/back input (20AC) at a preselected voltage when the bracelet electronics module scroll/pause/back switch (20G) is not depressed.

The bracelet electronics module scroll/pause/back switch (20G) functions to scroll in a forward or a backward direction the housing display indicia (20CA) on the bracelet electronics module alphanumeric display (20C).

The bracelet electronics module microcontroller (20A) further comprises a bracelet electronics module microcontroller transmit output (20AF) which is further connected to the bracelet electronics module LED/photodiode interface circuitry (20M)(not shown) and further electrically connected to the bracelet electronics module sending photodiode (20H) which functions to transmit electronic data from the bracelet electronics module microcontroller (20A). The bracelet electronics module microcontroller (20A) at the bracelet electronics module microcontroller receiver input (20AE) is further connected to the bracelet electronics module LED/photodiode interface circuitry (20M) (not shown) and further electrically connected to the bracelet electronics module receiver unit (20I) which functions to receive data and convert the data into a form recognizable by the bracelet electronics module microcontroller (20A). The bracelet electronics module receiver unit (20I) comprises a bracelet electronics module receiver unit pullup resistor (20IA) which is electrically connected at one distal end to the bracelet electronics module DC/DC converter (20D) and at the opposite distal end to a collector of the bracelet electronics module receiver unit transistor (20IB). The collector of the bracelet electronics module receiver unit transistor (20IB) is further electrically connected to a bracelet electronics module microcontroller receiver input (20AE). The bracelet electronics module receiver unit pullup resistor (20IA) functions to maintain the bracelet electronics module microcontroller receiver input (20AE) at a preselected voltage level in the absence of an incoming signal to the bracelet electronics module receiver unit (20I). The emitter of the bracelet electronics module receiver unit transistor (20IB) is electrically connected to an electrical ground. The base of the bracelet electronics module receiver unit transistor (20IB) is electrically connected to one distal end of a bracelet electronics module receiver unit bias resistor (20IC). The opposite distal end of the bracelet electronics module receiver unit bias resistor (20IC) is electrically connected to one distal end of the bracelet electronics module receiver unit receiver photodiode (20ID). The opposite distal end of the bracelet electronics module receiver unit receiver photodiode (20ID) is electrically connected to the bracelet electronics module DC/DC converter (20D). The bracelet electronics module receiver unit receiver photodiode (20ID) functions to receive a light wave input and convert it to a voltage.

The bracelet electronics module (20) is water proof.

Figure 5:
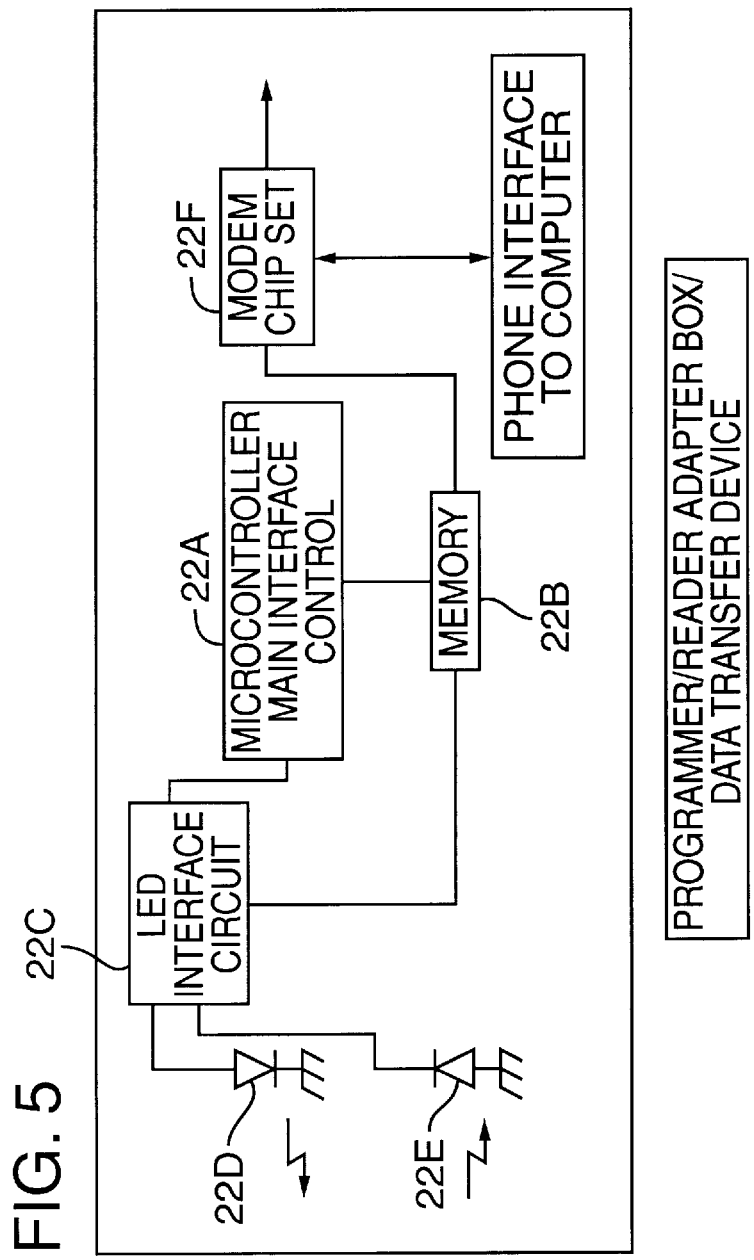
FIG. 5 is a block diagram of a data transfer device electronics module.
Figure 6:
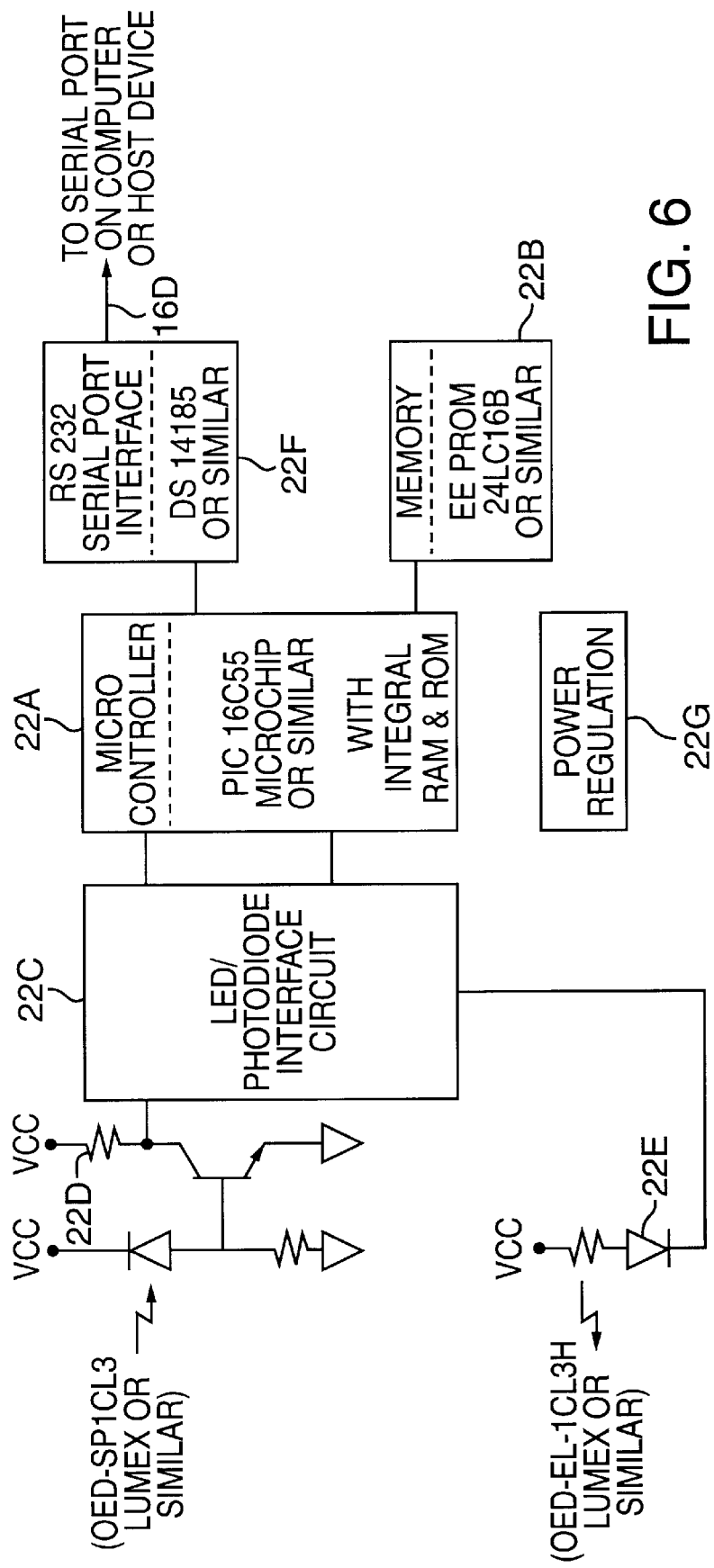
FIG. 6 is a schematic diagram of a data transfer device electronics module.

Lastly, referring to FIG. 5 which is a block diagram of a data transfer device electronics module (22) and to FIG. 6 which is a schematic diagram of a data transfer device electronics module (22). The data transfer device electronics module (22) comprises the data transfer device electronics module microcontroller (22A) which is electrically connected to the data transfer device electronics module memory (22B) functioning to store an operating program and data.

The data transfer device electronics module microcontroller (22A) is further electrically connected to data transfer device electronics module LED/photodiode interface circuitry (22C) which is further electrically connected to the data transfer device electronics module transmitter (22D) which functions to send data to the bracelet electronics module receiver unit (20I).

The data transfer device electronics module microcontroller (22A) is further connected to data transfer device electronics module LED/photodiode interface circuitry (22C) which is further electrically connected to the data transfer device electronics module data receiver (22E) functioning to receive data from the bracelet electronics module sending photodiode (20H).

The data transfer device electronics module microcontroller (22A) is further electrically connected to the data transfer device electronics module computer interface (22F) which functions to send and receive data to a data transfer device cable (16D). The data transfer device cable (16D) is electronically connected to a computer by a data transfer device cable connector (16DA).

It will be understood that each of the elements described above, or two or more together, may also find a useful application in other types of constructions differing from the type described above.

While the invention has been illustrated and described as embodied in a Medical Identification Bracelet worn around the wrist, it is not intended to be limited to the details shown as it also could be fashioned as a Medical Identification Pendant worn around the neck. It will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. A medical identification bracelet comprising:
   A) a housing, having a housing top side and a housing bottom side, the housing comprises:
      i) a housing back fastener fastened to the housing which secures the bracelet electronics module firmly in place,
      ii) a bracelet electronics module, contained within the housing, the bracelet electronics module comprises a bracelet electronics module microcontroller which is electrically connected to a bracelet electronics module memory functioning to store data, the bracelet electronics module microcontroller is further electrically connected to a bracelet electronics module alphanumeric display which functions to display bracelet electronics module alphanumeric display indicia selected from the bracelet electronics module memory, the bracelet electronics module microcontroller is further electrically connected to a bracelet electronics module DC/DC converter functioning to convert a voltage from a power source to a voltage usable by the bracelet electronics module, the bracelet electronics module microcontroller further comprises a bracelet electronics module microcontroller ON/OFF, backlight input which is electrically connected to a bracelet electronics module ON/OFF, backlight switch which functions to activate illumination of the bracelet electronics module alphanumeric display when the bracelet electronics module is turned on, and exhibit the bracelet electronics module alphanumeric display indicia which can be observed when ambient lighting is low, the bracelet electronics module microcontroller further comprises a bracelet electronics module microcontroller mode/send/receive input which is further electrically connected to a bracelet electronics module mode/send/receive switch connecting the bracelet electronics module microcontroller mode/send/receive input to an electrical ground, the bracelet electronics module mode/send/receive switch functions to switch the information depicted by the bracelet electronics module alphanumeric display indicia, the bracelet electronics module microcontroller further comprises a bracelet electronics module microcontroller scroll/pause/back input electrically connected to a bracelet electronics module scroll/pause/back switch connecting the bracelet electronics module microcontroller scroll/pause/back input to the electrical ground, the bracelet electronics module scroll/pause/back switch functions to scroll in a forward or a backward direction or to pause the housing display indicia on the bracelet electronics module alphanumeric display, the bracelet electronics module microcontroller further comprises a bracelet electronics module microcontroller transmit output which is further electrically connected to bracelet electronics module LED/photodiode interface circuit which is further connected to a bracelet electronics module sending photodiode functioning to transmit electronic data from the bracelet electronics module microcontroller, the bracelet electronics module microcontroller also comprises a bracelet electronics module microcontroller receiver input which is further electrically connected to a bracelet electronics module LED/photodiode interface circuit which is further connected to a bracelet electronics module receiver unit which functions to receive data and convert the data into a form recognizable by the bracelet electronics module microcontroller,
   B) a bracelet precious metal bar which comprises:
      i) a bracelet precious metal bar front name indicia which functions to display the user's name,
      ii) a bracelet precious metal bar front medical symbols which function to indicate that the medical identification bracelet contains personal medical information,
      iii) a holding means securely attached to opposite ends of the precious metal bar, the holding means functions to removably fasten the precious metal bar to the user's body,
   C) a data transfer device which comprises:
      i) a data transfer device housing which comprises a data transfer device front which is securely attached on one distal end to a front distal end of a data transfer device left side having a data transfer device left side slot therein, the data transfer device front on an opposite distal end is securely attached to a front distal end of a data transfer device right side having a data transfer device right side slot therein, the data transfer device right side slot and the data transfer device left side slot functions to removably fasten the bracelet electronics module therebetween, a back distal end of the data transfer device left side is securely attached to one distal end of a data transfer device back, the opposite distal end of the data transfer device back is securely attached to a back distal end of the data transfer device right side;
      ii) a data transfer device electronics module which comprises a data transfer device electronics module microcontroller electrically connected to a data transfer device electronics module memory that functions to store an operating program and data, the data transfer device electronics module microcontroller is further electrically connected to a data transfer device electronics module LED/photodiode interface circuit which is connected to a data transfer device electronics module transmitter which functions to send data to the bracelet electronics module receiver unit, the data transfer device electronics module microcontroller is further electrically connected to a data transfer device electronics module LED/photodiode interface circuit which is connected to a data transfer device electronics module data receiver functioning to receive data from the bracelet electronics module sending photodiode, the data transfer device electronics module microcontroller is further electrically connected to a data transfer device electronics module computer interface which functions to send and receive data to a data transfer device cable, the data transfer device cable is electronically connected to a computer by a data transfer device cable connector.

2. The medical identification bracelet as described in claim 1, wherein the fastening means securing the bracelet electronics module to the precious metal bar comprises a housing and housing back fasteners.

3. The medical identification bracelet as described in claim 1, wherein the holding means comprises a left holding means, one distal end of the left holding means is securely attached to one distal end of the precious metal bar, the opposite distal end of the left holding means is securely attached to a left holding means fastener, the opposite distal end of the precious metal bar is securely attached to one distal end of a right holding means, the opposite distal end of the right holding means is securely attached to a right holding means fastener, the left holding means fastener and right holding means fastener are removably fastened together.

4. The medical identification bracelet as described in claim 3 wherein the left holding means fastener and the right holding means fastener are selected from a group consisting of hook & loop, hook & eye, buckle, snaps, and button/hole.

5. The medical identification bracelet as described in claim 1, wherein the preselected groupings of information are selected from a group consisting of personal data, medical conditions, medications & dosages, allergies, insurance company information, next of kin, patient history, physician and pharmacy names and phone numbers, previous illnesses, blood type and pressure.

6. The medical identification bracelet as described in claim 1, wherein the bracelet electronics module receiver unit comprises a bracelet electronics module receiver unit pullup resistor which is electrically connected at one distal end to the bracelet electronics module DC/DC converter and at the opposite distal end to a collector of a bracelet electronics module receiver unit transistor, the collector of a bracelet electronics module receiver unit transistor is further electrically connected to a bracelet electronics module microcontroller receiver input, bracelet electronics module receiver unit pullup resistor functions to maintain the bracelet electronics module microcontroller receiver input at a preselected voltage level in the absence of an incoming signal to the bracelet electronics module receiver unit, the emitter of the bracelet electronics module receiver unit transistor is electrically connected to electrical ground, the base of the bracelet electronics module receiver unit transistor is electrically connected to one distal end of a bracelet electronics module receiver unit bias resistor, the opposite distal end of the bracelet electronics module receiver unit bias resistor is electrically connected to one distal end of a bracelet electronics module receiver unit receiver photodiode, the opposite distal end of the bracelet electronics module receiver unit receiver photodiode is electrically connected to the bracelet electronics module DC/DC converter, the bracelet electronics module receiver unit receiver photodiode functions to receive a light wave input and convert it to a voltage.

7. The medical identification bracelet as described in claim 1, wherein the bracelet electronics module microcontroller backlight input is electrically connected to one distal end of a bracelet electronics module first pull up resistor, the opposite distal end of the bracelet electronics module first pull up resistor is electrically connected to the bracelet electronics module DC/DC converter, the bracelet electronics module first pull up resistor functions to keep the bracelet electronics module microcontroller backlight input at a preselected voltage when the bracelet electronics module ON/OFF, backlight switch is not depressed.

8. The medical identification bracelet as described in claim 1, wherein the bracelet electronics module microcontroller mode/send/receive input is electrically connected to one distal end of a bracelet electronics module second pull up resistor, the opposite distal end of the bracelet electronics module second pull up resistor is electrically connected to the bracelet electronics module DC/DC converter, the bracelet electronics module second pull up resistor functions to keep the bracelet electronics module microcontroller mode/send/receive input at a preselected voltage when the bracelet electronics module mode/send/receive switch is not depressed.

9. The medical identification bracelet as described in claim 1, wherein the bracelet electronics module microcontroller scroll/pause/back input is electrically connected to one distal end of a bracelet electronics module third pull up resistor, the opposite distal end of the bracelet electronics module third pull up resistor is electrically connected to the bracelet electronics module DC/DC converter, the bracelet electronics module third pull up resistor functions to keep the bracelet electronics module microcontroller scroll/pause/back input at a preselected voltage when the bracelet electronics module scroll/pause/back switch is not depressed.

10. The medical identification bracelet as described in claim 1, wherein the housing is manufactured from materials selected from a group consisting of plastic, plastic composite, rubber, rubber composite, ceramic, plastic composite, metal, metal alloy, precious metal, gems, and wood.

11. The medical identification bracelet as described in claim 1, wherein the precious metal bar, left holding means, left holding means fastener, right holding means, and right holding means fastener are manufactured from materials selected from a group consisting of plastic, ceramic, plastic composite, metal, metal alloy, precious metal, gems, and wood.

12. The medical identification bracelet as described in claim 1, wherein the bracelet electronics module is water proof.

13. The medical identification bracelet as described in claim 1, wherein the bracelet electronics module scroll/pause/back switch when pressed by a user functions to control the scrolling of the preselected groupings of information across the bracelet electronics module alphanumeric display.

14. The medical identification bracelet as described in claim 1, wherein the bracelet electronics module mode/send/receive switch functions to switch between functions selected from a group consisting of display information, transmit data and receive data.

* * * * *